(12) United States Patent
Strzemiemski et al.

(10) Patent No.: US 6,534,078 B1
(45) Date of Patent: Mar. 18, 2003

(54) MICRO-ENCAPSULATED PEPPER-MUSTARD COMPOSITION AND METHODS OF USING THE SAME

(75) Inventors: Thomas M. Strzemiemski, Washington, DC (US); Fortunato J. Micale, Bethlehem, PA (US)

(73) Assignee: Natural Pest FX, Inc., WA (US)

( * ) Notice: Subject to any disclaimer, the term of this patent is extended or adjusted under 35 U.S.C. 154(b) by 0 days.

(21) Appl. No.: 09/419,657

(22) Filed: Oct. 18, 1999

(51) Int. Cl.⁷ .............................................. A01N 25/28
(52) U.S. Cl. ...................... 424/408; 424/406; 424/417; 424/736; 424/755; 424/760; 424/405; 424/45; 424/46; 514/918; 514/919; 514/920
(58) Field of Search ................................ 424/405, 408, 424/417, 406, 45, 46, 736, 755, 760; 514/918–920

(56) References Cited

U.S. PATENT DOCUMENTS

| | | | | |
|---|---|---|---|---|
| 4,696,822 A | * | 9/1987 | Matsumura et al. | ........ 424/490 |
| 4,911,928 A | * | 3/1990 | Wallach | ........ 424/450 |
| 5,145,675 A | | 9/1992 | Won | |
| 5,240,708 A | | 8/1993 | Plummer et al. | |
| 5,322,862 A | | 6/1994 | Kurata et al. | |
| 5,456,916 A | | 10/1995 | Kurata et al. | |
| 5,525,597 A | | 6/1996 | Hainrihar et al. | |
| 5,618,565 A | | 4/1997 | Thomas | |
| 5,711,953 A | | 1/1998 | Bassett | |
| 5,756,100 A | | 5/1998 | Martinez | |
| 5,788,975 A | * | 8/1998 | Laversanne et al. | ........ 424/417 |
| 5,876,739 A | | 3/1999 | Turnblad et al. | |
| 5,879,696 A | | 3/1999 | Blumberg | |
| 5,985,010 A | | 11/1999 | Etscorn et al. | |
| 6,051,233 A | | 4/2000 | Champon | |
| 6,139,857 A | | 10/2000 | Gaddini | |
| 6,143,288 A | | 11/2000 | Warren et al. | |
| 6,224,685 B1 | | 5/2001 | Gross et al. | |
| 6,228,355 B1 | | 5/2001 | Byrd, II et al. | |

FOREIGN PATENT DOCUMENTS

| | | | |
|---|---|---|---|
| JP | 7-76502 | * | 3/1995 |

OTHER PUBLICATIONS

Bauer et al (Abstract) Pestic Sci 55 (8) 831–842, 1999.*

* cited by examiner

*Primary Examiner*—Neil S. Levy

(57) ABSTRACT

A micro-encapsulated pepper-mustard composition which comprises positioning pepper and mustard mixtures within a cluster of surfactant molecules, i.e. micelles, dispersed in water. This micro-encapsulation process involves first forming the micelles in water by exceeding the given critical micelle concentration for either one, two, or three different surfactant types. The active ingredient, pepper and mustard, is then added to this mixture and subsequently emulsified into small liquid drops in order to facilitate swelling of the micelles by way of migration or diffusion of the active ingredient molecules through the water phase and into the micelles. The resulting encapsulated pepper and mustard is effectively stabilized by the surfactant molecules, and the resulting stabilized micro-encapsulated dispersion will not undergo phase separation.

12 Claims, No Drawings

MICRO-ENCAPSULATED PEPPER-MUSTARD COMPOSITION AND METHODS OF USING THE SAME

FIELD OF THE INVENTION

The present invention relates to a micro-encapsulated pepper-mustard composition that is useful as a soil treatment, insecticide, and as a repellant.

BACKGROUND OF THE INVENTION

For the most part, most commercially successful soil treatments and insecticides are manufactured from synthetic chemicals. In recent years, the public and the federal government have become acutely aware of the dangers that flow from these synthetic based soil treatments and insecticides. In short, they are highly toxic and because of the nature of their applications, find their way into streams, waterways and ground water. Because of that, they are deemed to be dangerous to the public at large.

There have been attempts at developing natural base compositions for treating soil and performing as an insecticide. For example, mustard and pepper combinations have been used in the past as insecticides and soil treatments. However, they have in large part been ineffective. This is principally because pepper and mustard compositions cannot be formulated in a water base, but have to be mixed with an oil base.

One of the major problems experienced with oil based mustard and pepper soil treatments and insecticides is phytotoxicity. Phytotoxicity is a problem which cannot be tolerated in any agricultural crop because it effectively kills even the healthiest crops. It is postulated that the oil base that is found in conventional mustard and pepper solutions tends to magnify the intensity of the heat from the sun as it strikes the plants. This intense heat has the effect of killing crops, such as tomatoes or severely damaging the crop such that it is of little value.

Another concern with mustard and pepper compositions that are found in oil based solution is that they are difficult to handle and apply. Both mustard and pepper extracts have been known to cause severe reactions in the human nervous system. A sensation of severe heat and extreme pain may occur if the oil base pepper and mustard composition is applied, even accidentally, to the skin. Because of this, these mustard and pepper compositions have proven themselves to be difficult in areas such as greenhouses and on crops where the workers must be in and around the plants shortly after application.

Therefore, there has been and continues to be a need for an effective naturally occurring composition that does not carry with it the drawbacks and shortcomings of synthetic chemicals, that will be practical and effective in agricultural applications, especially as a soil treatment or insecticide.

SUMMARY OF THE INVENTION

The present invention entails a micro-encapsulated pepper-mustard composition. Basically this composition comprises an emulsified mixture of pepper and mustard, a surfactant, and a water base. The surfactant basically forms an encapsulation around particles of the pepper-mustard mixture.

In formulating the micro-encapsulated pepper-mustard composition of the present invention, pepper and mustard, in a liquid form, is emulsified. One or more surfactants are mixed with a water base. The surfactant forms clusters of micelles. Thereafter the emulsified pepper-mustard mixture is mixed with the micelles, in the water base, with sufficient energy to drive particles of the pepper-mustard mixture into the micelles where they are encapsulated.

The micro-encapsulated pepper-mustard composition has significant utility and can be applied as a part of different methods. The primary advantage or utility of this invention is that it can be placed in water at high concentrations and applied as a water based system. For example, the micro-encapsulated pepper-mustard composition is effective as a soil treatment to kill nematodes. In addition, it is effective as an insecticide and as a self-defense composition or a repellant. Further, the micro-encapsulated pepper-mustard composition is effective as a paint additive to prevent and inhibit the growth of algae and mollusks from growing on boats and other objects exposed to water and moisture.

Other objects and advantages of the present invention will become apparent and obvious from a study of the following description which is merely illustrative of such invention.

DETAILED DESCRIPTION OF THE INVENTION

The present invention entails a micro-encapsulated pepper and mustard composition. The micro-encapsulated pepper-mustard composition comprises an emulsified pepper and mustard mixture combined with one or more surfactants and a water base. The surfactant or surfactants form encapsulations that surround and house small micron and submicron size particles of the active components, pepper and mustard.

Pepper in the form of a liquid extract is used for the composition. Various grades of pepper based on heat qualities are available commercially. Pepper utilized in a preferred composition would be extracted from fruit of pepper plants such as jalapeno, birdseye, cayenne or habanero. Although various heat grades may be used in the present composition, it is contemplated that heat grades of 2–5 million Scoville heat units would be preferred, in some formations. In lieu of the pepper, it is contemplated that horseradish may be substituted in the composition of the present invention. Horseradish, like pepper, would be extracted from horseradish plants.

Further, the mustard, like the pepper, is naturally occurring and can be purchased in the form of a purified liquid extract. It is contemplated that the mustard used in the present composition would be of a food grade.

As noted above, the pepper and mustard that form the active ingredients of the present composition are preferably naturally occurring and are taken from pepper and mustard plants. However, it is appreciated that synthetic versions of pepper and mustard may be used. Accordingly, when used herein, the terms pepper and mustard are intended to include not only naturally occurring pepper and mustard, but any and all synthetic or artificial versions of pepper and mustard.

In addition to the pepper, mustard, surfactant or surfactants, and water, the composition may be provided with a solvent. Although various solvents may be utilized, it is contemplated that citrus oil, sometimes referred to as d-Limonene, would be an acceptable solvent. The solvent being referred to here can be viewed as a part of the active ingredients, pepper and mustard. This is because the principal function of the solvent is to mix or combine the pepper and mustard together.

In a preferred composition of the micro-encapsulated pepper-mustard composition, the pepper, by weight, would comprise approximately 4–10% of the composition. Mustard, on the other hand, would comprise, by weight approximately 3–8% of the composition. The surfactant or surfactants would comprise, by weight, approximately 2–6% by weight of the composition. Further, the solvent that combines the pepper and mustard together would comprise, by weight, approximately 2–4% of the composition. The water constituting the base would in a preferred composition comprise, by weight, approximately 70–90% of the total composition.

In some embodiments, the percentage weights for the respective components of the composition may lie outside these preferred ranges. For example, it is contemplated that pepper may under certain circumstances, comprise, by weight, approximately 1–18% of the composition. Likewise under such circumstances mustard may comprise, by weight, approximately 1–12% of the composition. The solvent or the surfactant or surfactants may each under certain conditions comprise, by weight, 1–10% of the total composition. Finally, water, under certain conditions may comprise, by weight, approximately 60–99% of the total composition.

To formulate the micro-encapsulated pepper-mustard composition of the present invention, one or more surfactants are selected. In a preferred composition, two different surfactants such as block copolymers of propylene oxide and ethylene oxide and polyoxyethylene sorbitan monolaurate may be used. However, one, two, three or more surfactants can be utilized. Suitable surfactants for the micro-encapsulated pepper-mustard composition of the present invention include derivatives of capryl imidzoline, alkyl polyglycol ethers, polyoxyalkylene lanolins, block copolymers of propylene oxide and ethylene oxide, and polyoxyethylene sorbitan monolaurate.

After the surfactant or surfactants have been selected, they are dispersed in the water base. Surfactants selected for the present composition are made up of molecules that have a hydrophilic end group and a hydrophobic hydrocarbon tail. The hydrophilic group, of course, has a propensity for water while the hydrophobic tail possesses an aversion for water. Thus, above a certain concentration, the surfactant molecules tend to associate with one another in a group whereby the hydrophilic group is exposed to the water and are configured such that they form a generally circular or spherical configuration while the hydrophobic tails extend inwardly and associate with each other, perhaps in an intertwined relationship. Effectively, this forms clusters of surfactant molecules which are called micelles. It is postulated that the hydrophilic portion of the micelles forms a shell or a continuous mixture around an interior area that is occupied by the hydrophobic tails of the surfactant molecules. Thus, this creates or gives rise to a shell type structure even though it may not be continuous and would include tiny openings that will facilitate the active ingredients, pepper and mustard, migrating therethrough so as to be housed or encapsulated within the formed micelles.

After the surfactant or surfactants have been dispersed in the water base, then the active ingredients, the pepper and mustard can be added. In order to achieve encapsulation, the pepper and mustard mixture is emulsified. By emulsifying the pepper and mustard, the constituent particles thereof are made smaller and the surface area of the active ingredients is increased by way of the smaller drops or particles. It is contemplated that the emulsion process may even achieve phase separation between the particles of pepper and mustard. By emulsifying the pepper and mustard, the particles of these active ingredients are brought extremely close to the micelles and this has the effect of accelerating the diffusion process. That is, as the pepper and mustard particles are reduced in size and essentially form small drops, they tend to be in a position to more favorably move into and swell the micelles because of the hydrophobic attraction that exists in the interior of the micelles due to the hydrophobic nature of the tails of the surfactant molecules. Thus, it is postulated that in this process, the emulsified particles or droplets of pepper and mustard move from and through the water phase into a micro-encapsulated state where the size of the pepper-mustard encapsulations are on the order of 0.1–10 microns. It is appreciated that because of the low solubility of the pepper and mustard in water that one cannot stabilize these active ingredients at a useful concentration. So by encapsulating particles of the active ingredients, one is able to form a composition having a useful concentration of these active ingredients.

To effectively micro-encapsulate particles of the pepper and mustard in the micelles, it is required that significant energy be supplied through the emulsion process. It is contemplated that this can be achieved by a high speed, high energy mixing operation. It is also postulated that a simple mixing operation will not supply the necessary energy to drive the particles of emulsified pepper and mustard into the micelles. In a pilot operation conducted in the laboratory an ultrasonic high energy probe was used to generate sufficient energy to emulsify the particles of pepper and mustard and urge them into the micelles where they were micro-encapsulated. In commercial applications, anyone of a variety of commercial emulsifiers can be used to emulsify the pepper and mustard and effectively urge or cause the pepper and mustard molecules to migrate into the micelles where they are micro-encapsulated.

The micro-encapsulated pepper-mustard composition of the present invention has utility in a number of areas. First, the micro-encapsulated pepper-mustard composition is effective as a soil treatment to kill nematodes or pathogens/viruses, such as phytopthora or fusarium oxysporum, that attack roots of plants. In applying the micro-encapsulated pepper-mustard composition, it is contemplated that the combined concentration of the pepper and mustard in a particular application would be approximately 20,000–40,000 ppm. Of course, this concentration could vary depending upon the conditions of the soil to be treated and the concentration of the nematodes or pathogens within the soil. There are a number of ways in which the micro-encapsulated pepper-mustard composition can be applied to the soil. It can simply be applied directly to the top of the soil or it can be cultivated or tilled into the soil.

In one test conducted with the micro-encapsulated pepper-mustard composition of the present invention, a soil plot having some 20 plants was inoculated and infested with a pathogen, phytopthora. The micro-encapsulated pepper-mustard composition was applied to the test plot at a concentration of 20,000 ppm. After three weeks there was no evidence of phytotoxicity and 18 of the 20 plants were still alive. In associated control plots, also having 20 plants and inoculated and infested with approximately the same concentration of phytopthora, all 20 plants were killed or destroyed within a three week period, indicating that the 20,000 ppm concentration of the micro-encapsulated pepper-mustard composition was an effective soil treatment.

In addition to treating soils, the micro-encapsulated pepper-mustard composition is an effective insecticide. By applying the composition to the ground or to plants directly, insects are killed and the associated crop is protected. It is contemplated that a concentration of approximately 10,000 to 20,000 ppm of the active ingredients, pepper and mustard, in the micro-encapsulated composition would form an effective insecticide. However, it should be appreciated that other concentrations outside of these ranges may be required in order to be effective under certain field conditions.

A third application of the present invention entails packaging a pepper-mustard composition as an aerosol and utilizing the composition as a repellant. Note here, the pepper and mustard need not be micro-encapsulated. Both encapsulated and non-encapsulated forms of the pepper and mustard composition would be effective as a repellant. This, can be used in situations that call for exerting a formidable self-defense force or simply repelling an attacking dog. It is contemplated that the combined concentration of the pepper and mustard in an aerosol based repellant would be approximately 5,000 to 12,000 ppm. As above, it is appreciated that the concentration levels can be varied.

Another application of the present invention entails utilizing the pepper-mustard composition to treat edible materials, such as birdseed and vegetation, that might be prone to be eaten by animals such as squirrels and deer. More particularly, the micro-encapsulated pepper-mustard composition can be mixed with birdseed and it is postulated that this treatment will deter or prevent squirrels from eating the birdseed yet not adversely affect the desire of birds to consume the birdseed. In like manner, the same micro-encapsulated pepper-mustard composition can be sprayed or applied in other ways to flowers, shrubbery and other vegetation. This treatment will protect such vegetation from being consumed by animals such as deer,and the like.

Finally, the micro-encapsulated pepper-mustard composition can be used as a paint additive, especially as an additive to a latex paint. As a paint additive, it is postulated that the micro-encapsulated pepper-mustard composition would be effective to kill and deter the growth of algae and mollusks on the cured paint film applied to boats and other marine equipment and other objects and materials that are exposed to water and moisture.

From the foregoing specification, it is appreciated that by micro-encapsulating the pepper and mustard ingredients, that one is able to form a water base composition that will carry useful and effective concentrations of these active ingredients, and will permit the composition to be dispersed on soils and plants, for example, in such a manner that the active ingredients are uniformly distributed or dispersed. Thus it is appreciated that by micro-encapsulating the active ingredients that an efficient and effective composition is formed that has wide utility.

What is claimed is:

1. A micro-encapsulated capsicum-mustard composition comprising: capsicum extract; mustard extract; at least one surfactant: a water-base; and wherein the surfactant molecules form clusters of micelles and wherein the capsicum and mustard are emulsified, causing the capsicum and mustard molecules to migrate into the micelles so as to effectively encapsulate the capsicum and mustard molecules; wherein the composition comprises by weight approximately 1–30% of capsicum and mustard, approximately 70–98% water base, and approximately 1–8% surfactant or surfactants; and wherein the encapsulated particles of capsicum and mustard of are of size of approximately 0.1–10 microns.

2. The micro-encapsulated capsicum-mustard composition of claim 1 further including a solvent for combining the capsicum and mustard.

3. The micro-encapsulated capsicum-mustard composition of claim 2 wherein the solvent comprises citrus oil.

4. The micro-encapsulated capsicum-mustard composition of claim 1 wherein the surfactant is taken from the group consisting of capryl imidzolines, alkyl polyglycol ethers, polyoxyalkylene lanolins, block copolymers of propylene oxide and ethylene oxide, and polyoxyethylene sorbitan monolaurate.

5. The micro-encapsulated capsicum-mustard composition of claim 1 wherein the composition includes at least two surfactants.

6. The micro-encapsulated capsicum-mustard composition of claim 5 wherein the at least two surfactants include block copolymers of propylene oxide and ethylene oxide, and polyoxyethlyene sorbitan monolaurate.

7. The micro-encapsulated capsicum-mustard composition of claim 1 formed by dispersing the at least one surfactant in the water base so as to give rise to the clusters of micelles; and urging the capsicum and mustard molecules into the micelles by emulsifying the capsicum and mustard.

8. The micro-encapsulated composition of claim 1 wherein the composition is a repellant and useful in self defense and against attacking animals.

9. The micro-encapsulated repellant of claim 8 wherein the composition is packaged in the form of an aerosol.

10. The micro-encapsulated composition of claim 1 wherein the micro-encapsulated capsicum-mustard composition forms a pesticide.

11. The micro-encapsulated composition of claim 1 wherein the composition forms a paint additive for killing, repelling, or inhibiting the growth of algae on mollusks or cured paint films.

12. The micro-encapsulated composition of claim 10 wherein the composition is utilized for treating soil and killing nematodes and pathogens within soil.

* * * * *

UNITED STATES PATENT AND TRADEMARK OFFICE
CERTIFICATE OF CORRECTION

PATENT NO.    : 6,534,078 B1
DATED         : March 18, 2003
INVENTOR(S)   : Thomas M. Strzemienski and Micale J. Fortunato It is certified that error appears in the above-identified patent and that said Letters Patent is hereby corrected as shown below:

<u>Title page,</u>
Item [75], please change "Strzemiemski" to -- Strzemienski --.

Signed and Sealed this

Nineteenth Day of August, 2003

JAMES E. ROGAN
*Director of the United States Patent and Trademark Office*